United States Patent [19]

Jachimowicz

[11] 4,317,932

[45] Mar. 2, 1982

[54] PREPARATION OF SECONDARY AMINES

[75] Inventor: Felek Jachimowicz, Columbia, Md.

[73] Assignee: W. R. Grace & Co., New York, N.Y.

[21] Appl. No.: 123,822

[22] Filed: Feb. 22, 1980

[51] Int. Cl.$^3$ ............................................. C07C 85/18
[52] U.S. Cl. ..................... 564/445; 564/305; 564/306; 564/309; 564/336; 564/340; 564/343; 564/346; 564/355; 564/374; 564/378; 564/389; 564/391; 564/395; 564/396; 564/399; 564/401; 564/408; 564/446; 564/447; 564/467
[58] Field of Search ........... 260/585 D, 583 R, 583 P; 564/467, 305, 336, 408, 445, 467

[56] References Cited

U.S. PATENT DOCUMENTS

| | | | |
|---|---|---|---|
| 2,381,472 | 8/1945 | Teter | 260/585 D X |
| 2,417,893 | 3/1947 | Teter | 260/585 D X |
| 2,497,310 | 2/1950 | Larson | 260/585 D |
| 3,513,200 | 5/1970 | Biale | 260/583 R |
| 3,726,926 | 4/1973 | Brown et al. | 260/583 R X |
| 3,758,586 | 9/1973 | Coulson | 260/583 R |
| 3,947,458 | 3/1976 | Iqbal | 260/563 R X |
| 4,096,150 | 6/1978 | Berthoux et al. | 564/467 |
| 4,107,079 | 8/1978 | Chevallier et al. | 260/583 R X |
| 4,119,652 | 10/1978 | Knowles et al. | 260/583 R X |
| 4,130,590 | 12/1978 | Hobbs et al. | 260/585 D |
| 4,179,469 | 12/1979 | Imai | 260/583 P X |

FOREIGN PATENT DOCUMENTS

| | | | |
|---|---|---|---|
| 891067 | 3/1962 | United Kingdom | 260/585 D |
| 1072796 | 6/1967 | United Kingdom | 564/467 |
| 1178308 | 1/1970 | United Kingdom | 564/467 |
| 1378185 | 12/1974 | United Kingdom | 564/467 |
| 1468773 | 3/1977 | United Kingdom | 564/467 |
| 2044757 | 10/1980 | United Kingdom | 564/467 |

OTHER PUBLICATIONS

Houben-Weyl, "Methoden der Organischen Chemie", 4th Ed., vol. 11/1, pp. 994–999 (1957).

Primary Examiner—John Doll
Attorney, Agent, or Firm—Philip M. Pippenger; Howard J. Troffkin

[57] ABSTRACT

A process for forming amines by contacting, in a liquid media, an olefinic compound, carbon monoxide, water, and ammonia in the presence of a rhodium atom containing compound selected from metallic rhodium, rhodium salts, rhodium oxides, and rhodium carbonyls and ligands thereof at a temperature of from 50° to 250° C. and at a pressure of from about 10 to about 300 atmospheres.

8 Claims, No Drawings

PREPARATION OF SECONDARY AMINES

BACKGROUND OF THE INVENTION

The present invention is directed to a process of forming secondary amines from olefinic hydrocarbons and ammonia. The resultant product can be a lower hydrocarbyl amine or a fatty amine, as desired, depending of the starting olefin.

Lower aliphatic amines are generally prepared by one of four commercial processes. In one process, alcohols are reacted with ammonia in the presence of a dehydrating agent, such as alumina to produce a primary, secondary or tertiary amine depending on the ratio of reactants used. A second commercial method comprises reacting an alcohol with ammonia in the presence of hydrogen and a hydrogenation catalyst, such as nickel. This method normally produces a mixture of amines.

A third method requires the reaction of aldehydes and butanes with ammonia and hydrogen in the presence of a hydrogenation catalyst such as copper or nickel. Again, the product is a mixture of amines. Finally, the commercial method of forming fatty amines is accomplished by reacting a fatty acid or its ester with ammonia to form the nitrile and then hydrogenating the nitrile to form the amine. Secondary amines require the exclusion of water, high reaction temperatures and venting of residual ammonia.

Catalytic alkylation of organic amines with an olefin, carbon monoxide and hydrogen to form tertiary amines was initially disclosed by Reppe in *Experiention*, Vol. 5, p. 93 (1949); German Pat. No. 839,800 (1952); and *Liebigs Ann. Chem.*, Vol. 582, p. 148 (1953). The process had limited value due to the required use of large quantities of iron or nickel carbonyls as the catalyst, the slow rate of reaction and poor yields. Further, the process was directed at the formation of tertiary amines.

Similarly, U.S. Pat. Nos. 2,422,631; 3,234,283; 3,513,200; and 4,096,150 each disclose systems which permit catalytic alkylation of certain amines to form tertiary amino compounds.

It is highly desired to find a simple one step process which is capable of forming secondary amines and, further, which is capable of forming fatty secondary amines having either odd and even number of carbon atoms per hydrocarbyl chain.

SUMMARY OF THE INVENTION

Secondary amines formed in accordance with the presently described invention are highly desired materials known to be useful as surfactants, flocculating agents, softeners, as well as intermediates in the formation of dyes and other organo materials. Conventional methods of forming the desired secondary amines require multi-step synthesis methods which are both difficult and costly.

The present invention is directed to a one step catalytic method of forming the desired secondary amine in high yields by contacting, in a liquid media, an olefinic compound, carbon monoxide, water and ammonia in the presence of a catalytic amount of rhodium compound selected from metallic rhodium, rhodium salts, oxides, carbonyls, phosphines or ligands. The reaction is carried out in an inert solvent at temperatures of from about 50° to 250° C. and at a pressure of from about 30 to about 300 atmospheres.

DETAILED DESCRIPTION

The subject invention is directed to a new and novel one step, catalytic method of forming organo secondary amines by contacting, in an inert solvent, an olefinic compound with water, carbon monoxide and ammonia in the presence of certain rhodium compounds as the catalyst, as more completely described hereinbelow.

The olefinic compounds useful in forming the subject secondary amines can be any $C_2$ to $C_{20}$ hydrocarbons having at least one olefinic group therein. It is preferred that the olefinic compound contains a single olefinic group and further preferred that the olefinic group is terminally positioned. The olefinic compound can have alicyclic, aromatic or acyclic hydrocarbyl groups attached to the olefinic moiety of the compound. Examples of such compounds are ethylene, propylene, butene-1, butene-2, pentene-2, 2-methylbutene-1, hexene-1, octene-3, 2-propylhexene-1, decene-2, dodecene-1, tetradecene-5, octadecene-1, p-methyl styrene, vinyl cyclohexane, allyl cyclohexane, styrene, alpha methyl styrene, p-vinyl cumene, allyl benzene, cyclohexene, cyclopentene, amyl cyclohexene, cyclooctene and the like. The olefinic compound can also be substituted with a group or groups which are inert with respect to the present reaction such as hydroxyl, carboxyl, tertiary amino, thio, and the like. Examples of substituted olefinic compounds are p-dimethylamino styrene, crotonyl alcohol, allyl phenol and the like. The particular olefinic compound used will depend, of course, on the nature of the resultant amine desired.

In forming the subject secondary amine by the presently disclosed process it is to be understood that the number of carbon atoms on each of the resultant chains shall be more than the carbon atoms in the olefinic compound used. One can readily form a fatty amines, including those having an odd number of carbon atoms in each chain, by using an even numbered carbon atom containing olefin as a starting reactant, such as dodecene-1, tetradecene-1, octadecene-1 and the like. It is well known that certain classes of compounds, such as amines, alcohols, olefins, or carboxylic acids are normally found or formed as even numbered carbon atom containing compounds. Odd numbered compounds, such as odd numbered fatty amines are, on the contrary, unavailable or, at best, not readily available. The present invention is a unique method of forming such unavailable or difficult to obtain odd number carbon atom containing fatty amines from readily available even number carbon atom olefins in a straight forward, one step process.

The present invention is directed to a unique process of forming secondary amines. The process requires the utilization of certain critical reactants which are ammonia as the nitrogen source, water as the hydrogen source and a rhodium compound, as described below, as the catalyst.

The nitrogen source is required to be ammonia which can be either in liquid or gaseous form and can be either anhydrous or as an aqueous solution. It has been unexpectedly found that the use of ammonia, in combination with the other required agents, produces secondary amines in good yields.

It has been unexpectedly found that water acts as an effective hydrogen source in the subject process. The use of water, incidentally, does not have the detrimental safety problems associated with hydrogen gas. Water can be used, if desired, in combination with hydrogen gas although poorer yields of the desired product and safety problems complicate the reaction. Water should, therefore, be used alone or with only a minor amount of hydrogen. Because the presence of water has unexpectedly been found to cause the production of the desired secondary amines, it is to be understood that the other reactants and the liquid medium used need not be in a dry state.

The reaction is performed under liquid phase conditions. Any suitable organic liquid can be employed which is inert to the reaction conditions, the reactants, the catalyst and the products. Examples of suitable solvents that can be used in accordance with this invention include hydrocarbons such as the aromatics, aliphatics or alicyclic hydrocarbons, ethers, esters, etc.

Examples of suitable hydrocarbons that can be employed as the solvent include aromatic hydrocarbons such as benzene, toluene, xylene, ethyl benzene, tetraline, etc; aliphatic hydrocarbons such as butane, pentane, isopentane, hexane, isohexane, heptane, octane, isooctane, naphtha, gasoline, kerosene, mineral oil, etc.; alicyclic hydrocarbons, such as cyclopentane, cyclohexane, methylcyclopentane, decalin, indane, etc.

Ethers can also be employed as the reaction solvent, such as diisopropyl ether, di-n-butyl ether, ethylene glycol diisobutyl ether, methyl o-tolyl ether, ethylene glycol dibutyl ether, diisoamyl ether, methyl p-tolyl ether, methyl m-tolyl ether, dichloroethyl ether, ethylene glycol diisoamyl ether, diethylene glycol diethyl ether, ethylbenzyl ether, diethylene glycol diethyl ether, diethylene glycol dimethyl ether, ethylene glycol diethyl ether, ethylene glycol diphenyl ether, triethylene glycol diethyl ether, diethylene glycol di-n-hexyl ether, tetraethylene glycol dimethyl ether, tetraethylene glycol dibutyl ether, etc.

Various esters can also be employed as the solvent, such as ethyl formate, methyl acetate, ethyl acetate, n-propyl formate, isopropyl acetate, ethyl propionate, n-propyl acetate sec-butyl acetate, isobutyl acetate, ethyl-n-butylate, n-butyl acetate, isoamyl acetate, n-amyl acetate, ethyl formate, ethylene glycol diacetate, glycol diformate, cyclohexyl acetate, furfuryl acetate, isoamyl n-butyrate, diethyl oxalate, isoamyl isovalerate, methyl benzoate, diethyl malonate, valerolactone, ethyl benzoate, methyl salicylate, n-propyl benzoate, n-butyl oxalate, n-butyl benzoate, diisoamyl phthalate, dimethyl phthalate, diethyl phthalate, benzyl benzoate, n-butyl phthalate, etc. A preferred class of ester solvents includes the lactones, e.g., butyrlactone, valerolactone and their derivatives having lower ($C_1-C_5$) alkyl substituents.

Alcohols can also be employed as a reaction solvent. Preferably, tertiary alcohols, such as t-butyl or t-amyl alcohol, are employed although $C_1-C_8$ primary and secondary alcohols can also be employed.

Tertiary amines can also be employed as the reaction solvent, the nitrogen atom, by definition, being substituted with three hydrocarbyl groups which are inert with respect to the reaction, such as, for example, alkyl, aryl, alkaryl, aralkyl groups and the like. Examples of suitable tertiary amines include triethylamine, tripropylamine, triisobutylamine, trihexylamine, triheptylamine, triamylamine, dibenzyl ethylamine, dibutyl ethylamine, dimethyl pentylamine, diphenyl ethylamine, diphenyl methylamine, dimethyl aniline, pyridine, dimethyl pyridine, methoxy pyridine, methyl pyrrolidine, ethyl pyrrolidine and the like. The preferred solvents are the tertiary amines and, especially, pyridine, aniline, substituted pyrrolidine and its derivatives.

The reaction can also be carried out in liquid ammonia as the solvent. The ammonia can be present in large excess with respect to the other required reactants.

The particular solvent to be used will depend on its ability to remain in the liquid state at both ambient and at reaction conditions to facilitate the mixing of the components, its solvating ability with respect to at least some of the reactants, and its ease of handling, as can be readily determined by the artisan.

The reaction is performed under relatively mild conditions including temperatures from about 80° to about 250° C.; preferably from about 100° to about 200° C. Sufficient pressure should be used to maintain the reaction medium in a liquid phase. The reaction is carried out at pressures of from about 30 to about 300 atmospheres and, preferably, from about 30 to 100 atmospheres. Since the reaction is exothermic, the temperature can be maintained by suitable cooling of all or a portion of the reaction zone contents. The pressure can be maintained by the pressure of the carbon monoxide and, when used, hydrogen supplied to the reaction zone. If desired, a suitable inert gas, such as nitrogen, can also be charged to the reaction zone to supplement the partial pressures of the reaction gases.

The ratio of the reactants can be widely varied. The mole ratio of carbon monoxide to the hydrogen source should be at least about 3:1. Higher ratios, such as 5:1 and above, are preferred. The carbon monoxide can be used in excess to form sufficient pressure required in the reaction zone, as described above. The mole ratio of hydrogen source to ammonia should be at least 1:1. Finally, the ratio of olefinic bond contained in the olefinic compound to ammonia should be at least 2:1.

The catalyst required to aid in the formulation of the desired secondary amine compounds comprises rhodium compounds selected from elemental rhodium, rhodium salts, rhodium oxides, rhodium carbonyls, rhodium ligands as described herein below. The preferred catalysts are formed from rhodium compounds in which the rhodium atom is the plus one valence state. The exact chemical and physical composition of the entity which acts as the catalyst for the subject reaction is not known with certainty because of the possible restructuring and/or interaction of the rhodium compound used and the reactants contained in the reaction zone. Whether the rhodium compounds described herein directly act as the catalyst or as the precursor for the catalyst entity which causes the presently desired aminomethylation is immaterial. The subject rhodium compounds will be referred herein as the "catalyst" as they have unexpectedly been found to aid directly and/or indirectly in the formation of desired secondary amines by the present one-step process and to give the desired product in high yields.

The rhodium compounds which are useful in the subject invention must have some degree of solubility in the liquid media in which the subject aminomethylation is to take place. The choice of liquid media and/or catalyst to be used in a particular reaction so that the catalyst has some degree of solubility can be readily determined by those skilled in the art using conventional methods.

The catalyst found useful in the subject process can be a rhodium salt of an inorganic acid such as, for example rhodium chloride, rhodium nitrate, rhodium sulfate, rhodium perchlorate and the like or of an organic acid such as rhodium acetate and the like. The rhodium salts are well known commercial products formed conventionally by the reaction of rhodium oxide with an acid. The salt can be used in its anhydrous state or as a hydrated salt. The hydrated salts are preferred.

The catalyst of the subject process can be a rhodium ligand. The ligand can be formed in coordination with rhodium in any one of its valence states; that is of zero or plus 1, 2 or 3. The ligand moiety is formed from chemical moieties which contain unshared electrons such as atoms selected from nitrogen, oxygen, phosphorous or sulfur or which contains unsaturation. The ligand can be in the form of a carbonyl; an olefin such as ethylene, butene and the like; diolefines such as norbornodiene, cyclooctadiene-1,5 and the like; aliphatic aromatic, aryl aliphatic phosphites, such as triethyl phosphite, tributyl phosphite, trimethyl phosphite, triphenyl phosphite, dimethylphenyl phosphite, tritolyl phosphite, tribenzyl phosphite, ditolyl phenyl phosphite, and the like; aliphatic and cyclic ethers such as dimethyl and diethyl oxide, dioxane, dialkyl ether glycols, acetyl acetone and the like; primary, secondary, and tertiary amines which contain alkyl, aryl, alkaryl, arallayl cycloalkyl groups or mixtures thereof such as trimethyl amine, diethyl amine, toluidine and the like; heterocyclic bases such as pyridine, bypyridine and the like; ammonia; sulfides such as dialkyl, diaryl, alicyclic heterocyclic sulfides and the like; and mixtures of said ligand components with rhodium. When the ligand is formed from uncharged ligand components with charged rhodium, the compound is formed into a stable neutral state with an anion such as a chloride perchlorate, nitrate, hexaflourophosphate and the like.

The catalyst materials which are useful in the subject process can be generically described by the formula:

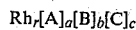

$Rh_r[A]_a[B]_b[C]_c$ wherein A represents an anion of an inorganic salt such as nitro, sulfo, halo, especially chloro, and the like; B represents a chemical moiety containing an entity having at least one pair of unshared electrons such as carbonyl, olefin, phosphite, ethers, amines, sulfides and mixtures thereof; C represents an anion capable of forming a neutral compound, such as chloride, hexaflourophosphite or the like; a, b and c each represent whole integers including 0 and r is an integer of one or greater.

The ligand may be added directly to the reaction medium and/or introduced into the medium as a complex of the ligand precursor with the rhodium salt, chelate, hydride or carbonyl. For example, the appropriate precursor of the desired ligand can be introduced into the reaction zone with a rhodium precursor such as, for example rhodium oxide, a rhodium carbonyl as dirhodium dichloro tetracarbonyl, and the like.

The rhodium compound useful in the present invention can be metallic rhodium. The metallic rhodium can be in any form such as a powder ribbon, or coated on an inert support. The inert support can be any conventional catalytic support as are well known such as formed from alumina, carbon, or a metal oxide, as, for example, an alkali or alkaline earth metal oxide and the like. The coating of metallic rhodium can be done by vapor disposition or other conventional methods and should be present in from about 2 to 8 percent by weight of the inert support. Metallic rhodium has, per se, substantially no degree of solubility in the liquid media contemplated for use but, it is believed that metallic rhodium reacts with some of the components in the reaction zone to form a soluble product which actually causes the desired aminomethylation to proceed. The metallic rhodium is, most probably, a precursor for the actual catalytic entity of the subject process.

The catalyst has been found to be effective to cause the formation of the desired polymeric polyamines as described above when used in a molar ratio of rhodium atom to olefin bond of from about $1\times10^{-4}$ to $2.5\times10^{-3}$ and preferably from about $1\times10^{-4}$ to $1\times10^{-3}$. The most preferred range from both effectiveness and economy is from $5\times10^{-4}$ to $1\times10^{-3}$. Although greater amounts of catalyst can be used, such has not been found required.

The rhodium catalysts found useful in the subject invention may be used in combination with other metal complexes which are known to cause aminomethylation as for example iron or cobalt carbonyl complexes and the like, although poorer results are normally obtained. It is, therefore, preferred that the rhodium catalyst is the sole or major catalyst used in the subject reaction.

The preferred rhodium catalysts are those which have rhodium in its plus 1 valence state and has been complexed with a carbonyl or diolefin or both.

The process is carried out by contacting the above described reactants and the catalyst in a vessel which is preferably adapted for gas injection, agitation and heating. The liquid media is first introduced followed by the monomeric olefinic containing compound and the rhodium catalyst. Water is added along with the other components. When ammonia is not used as the liquid media, it is added to the reaction vessel either as a gas or liquid. The reaction is carried out under elevated temperature and pressure. The vessel is closed and charged to a specific pressure with carbon monoxide alone or aided by the addition of an inert gas. The reactor and its contents are maintained at the desired elevated temperature for a sufficient period to cause the formation of the desired secondary amine which is normally accomplished in a period of time from about 15 minutes to about 10 hours with from about 30 minutes to 5 hours being sufficient and preferred in most instances. The vessel is then cooled and, where appropriate, degassed and the polymeric product is recovered by standard technique, such as by precipitation in a non-solvent, extraction and drying under vacuum. The resultant product may be a mixture of secondary amine with minor amounts of primary and tertiary amine. Separation can be accomplished by standard techniques such as distillation or fractional precipitation. The quantity of desired product can be determined by standard analytical techniques.

The following examples are for illustrative purposes only and are not meant to be a limitation on the subject invention except as indicated in the appended claims. All parts and percentages are by weight unless otherwise indicated.

EXAMPLE I

Into a 180 ml stainless steel rocking autoclave was charged 10.13 parts cyclohexene, 23.9 parts liquid ammonia, 4.5 parts water, 16.4 parts N-methyl pyrrolidine with 0.071 part rhodium oxide. The autoclave was sealed and charged to 1600 psig with carbon monoxide at 25° C. The autoclave was placed in an oil shaker bath and maintained at 170° C. for 4 hours.

The autoclave was cooled, degassed and the product was removed from the autoclave by washing with diethyl ether. The ether washings were collected and vacuum evaporated. The product was analyzed to be predominantly secondary amine having small amounts of primary and tertiary amine by-products. The mole ratio of secondary to primary amine was 27 and the mole rate of secondary to tertiary amine was 13.

EXAMPLE II

The procedure of Example I is repeated except that the rhodium oxide catalyst is replaced by tris(dimethylphenylphosphine) norbornadiene rhodium(I) hexafluorophosphate, $Rh_6(CO)_{16}$, $Rh\ Cl(C_5H_5N)_3$, $Rh(CO)_2(C_5H_7O_2)$ and $[Rh\ Cl(C_7H_8)]_2$, all commercially obtained. The resultant product is predominantly secondary amine similar to that obtained in Example I.

EXAMPLE III

The procedure of Example I above is repeated except that the cyclohexene is substituted with n-hexane. The product is analyzed to be predominantly the secondary amine diheptylamine with minor amounts of primary and tertiary amine.

EXAMPLE IV

The procedure of Example I is repeated except that the olefin is commercially obtained dodecene. The resultant product is analyzed to be di(tridecyl)amine, an odd carbon atom chain containing secondary amine.

Wile the invention has been described in connection with certain preferred embodiments, it is not intended to limit the invention to the particular forms set forth, but, on the contrary, it is intended to cover such alternatives, modifications and equivalents as defined by the appended claims.

What is claimed:

1. A process of forming secondary amino compounds comprising contacting, in a reaction zone, an inert liquid media, an olefinic compound, carbon monoxide, ammonia and water as the hydrogen source at a temperature of from about 50° to 250° C. and at a pressure of from about 30 to about 300 atmospheres in the presence of a catalytic amount of a catalyst consisting essentially of a rhodium atom containing compound selected from metallic rhodium, rhodium salts, rhodium carbonyls, rhodium oxides and ligands thereof; and recovering the formed secondary amine product.

2. The process of claim 1 wherein the rhodium compound contains a ligand moiety, said ligand moiety contains at least one atom selected from oxygen, sulfur, phosphorus, nitrogen or olefinic unsaturation.

3. The process of claim 1 wherein the catalyst is a rhodium atom containing compound having the general formula:

$$Rh_r[A]_a[B]_b[C]_c$$

wherein A represents halo, nitro, sulfo; B represents a chemical moiety containing at least one pair of unchared electrons selected from carbonyls, olefins, phosphites, ethers, amines, sulfides and mixtures thereof; and C is a neutral compound forming anion, r is a whole integer of 1 or greater and a, b and c are each whole integers including zero.

4. The process of claim 1 wherein the olefinic compound is a $C_2$ to $C_{20}$ monoolefin.

5. The process of claim 1 wherein the rhodium compound is present in an amount such that the molar ratio of rhodium atom to olefin bond is from about $1 \times 10^{-4}$ to $2.5 \times 10^{-3}$.

6. The process of claim 4 wherein the pressure is from about 30 to 100 atmospheres.

7. The process of claim 4 wherein the molar ratio of carbon monoxide to hydrogen source is at least about 1 to 1; of hydrogen source to ammonia is at least 1:1; and of olefin bond to ammonia is at least 2:1.

8. The process of claim 1, 5 or 7 wherein further a metal carbonyl selected from iron carbonyl and cobalt carbonyl is present in said reaction zone in minor amounts based on the weight of the weight of rhodium catalyst.

* * * * *